United States Patent [19]
Perry

[11] Patent Number: 5,011,780
[45] Date of Patent: Apr. 30, 1991

[54] IN VITRO EMBRYO CULTURE TECHNIQUE

[75] Inventor: Margaret M. Perry, Edinburgh, Scotland

[73] Assignee: The Agricultural and Food Research Council, London, England

[21] Appl. No.: 208,366

[22] Filed: Jun. 17, 1988

[30] Foreign Application Priority Data

Jun. 19, 1987 [GB] United Kingdom ............... 8714426

[51] Int. Cl.[5] ............................................. C12N 15/00
[52] U.S. Cl. ..................................... 435/317.1; 800/2; 800/DIG. 6; 435/240.2; 119/68
[58] Field of Search ..................... 800/1, 2, DIG. 6; 435/240.2, 317.1

[56] References Cited

PUBLICATIONS

Beadle, B. W., et al., Composition of the uterine secretion of the domestic fowl, Poultry Science, 17:498–504, 1938.
Romanoff, A. L., Cultivation of the early chick embryo in vitro, The Anatomical Record, 87(4):365–369, 1943.
Hamburger, V. and H. L. Hamilton, A Series of Normal Stages in the Development of the Chick Embryo, Journal of Morphology, 88:49–67, 1951.
New, D. A. T., The formation of Sub-Blastodermic Fluid in Hens's Eggs, Journal of Embryology and Experimental Morphology, 4:221–227, 1956.
News, D. A. T., A Critical Period for the Turning of Hens' Eggs, Journal of Embryology and Experimental Morphology, 5:293–295, 1957.
New, D. A. T., The Culture of Vertebrate Embryos, Chapter 3, Academic Press Inc. (London), pp. 47–98, 1966.
Leonard, E. M., The Accumulation of Minerals in the Avian Oviduct, Ph.D. Thesis, Univ. of Edinburgh, pp. 94–97, Dated Aug. 1968.
Davidson, M. F., and M. H. Draper, The Accumulation of Glucose in the White of the Egg of the Hen, Journal of Physiology, 202:119–120P, 1969.
Wangensteen, O. D., and H. Rahn, Respiratory Gas Exchange by the Avian Embryo, Respiratory Physiology, 11:31–45, 1970–1971.
Sauveur, B., and P. Mongin, Etude Comparative du Fluide Uterin et de L'albument de L'oeuf in Utero Chez la Poule, Annales de Biologie Animale, Biochemie, Biophysique, 11(2):213–224, 1971.
Howarth, B., Jr., An Examination for Sperm Capacitation in the Flow, Biology of Reproduction, 3:338–341, 1971.
Kochav, S., and H. Eyal-Giladi, Bilateral Symmetry in Chick Embryo Determination by Gravity, Science, 171:1027–1029, 1971.
Dawes, C. M., Acid–Base Relationships Within the Avian Egg, Biol. Rev., 50:351–371, 1975.
Kochav, S., et al., From Cleavage to Primitive Streak Formation: a Complementary Normal Table and a New Look at the First Stages of the Developement of the Chick. II. Microscopic Anatomy and Cell Population Dynamics, Developmental Biology, 79:296–308, 1980.
Dunn, B. E., et al., Effects of Varying Chamber Construction and Embryo Pre-Incubation Age on Survival and Growth of Chick Embryos in Shell-less Culture, The Anatomical Record, 199:33–43, 1981.
Callebaut, M., Autoradiographic Demonstration of the Penetration of Albumen–Derived Material Through the Viteline Membrane Into the Egg Yolk, Exterior to the Avian Biastoderm, Poultry Science, 62:1657–1659, 1983.

(List continued on next page.)

Primary Examiner—Elizabeth C. Weimar
Assistant Examiner—Jasemine C. Chambers
Attorney, Agent, or Firm—Christensen, O'Connor, Johnson & Kindness

[57] ABSTRACT

Avian embryos may be cultured in vitro up to blastoderm formation, during embryonic morphogenesis and/or during embryonic growth to hatch. The invention may have applications not only in the genetic engineering of poultry, but also in the investigation of fundamental mechanisms of avian development and in the study of deleterious traits. Moreover, it may afford a desirable alternative to surgical intervention in the laying hen.

1 Claim, 3 Drawing Sheets

OTHER PUBLICATIONS

Olszanska, B., et al., Effect of Spatial Position of Uterine Quail Blastoderms Cultured in Vitro on Bilateral Symmetry Formation, Roux's Archives of Developmental Biology, 193:108-110, 1984.

Ono, T., and N. Wakasugi, Mineral Content of Quail Embryos Cultured in Mineral-Rich and Mineral-Free Conditions, Poultry Science, 63:159-166, 1984.

Crittenden, L. B., and D. W. Salter, Gene Insertion: Current Progress and Long-Term Goals, Avian Diseases, 30(1):43-46, 1985.

Freeman, B. M., and L. I. Messer, Genetic Manipulation of the Domestic Fowl: a Review, World's Poultry Science Journal, 41(2):124-133, 1985.

Rowlett, K., and K. Simkiss, The Surrogate Egg: Birds are Suitable Subjects for Genetic Engineering, Because We Can Now "Reinvent" the Egg, New Scientist, 1469:42-44, 1985.

Perry, M. M., Embryo Manipulation in Poultry, 27th British Poultry Breeders Roundtable Conference, Edinburgh, 25-27 Sep. 1985, pp. 1-10, 1986.

Perry, M. M., Embryo Manipulation in Poultry, Edinburgh Centre of Rural Economy, 39th Annual Report, p. 17-25, 1986.

Perry, M. M., Nuclear Events From Fertilization to the Early Cleavage Stages in the Domestic Fowl (*Gallus Domesticus*), J. Anat., 150:99-109, 1987.

Rowlett, K., and K. Simkiss, Explanted Embryo Culture: in Vitro and in Ovo Techniques for Domestic Fowl, British Poultry Science, 28:91-101, 1987.

Perry, M. M., A Complete Culture System for the Chick Embryo, Nature, 331(6151):70-72, 7 Jan. 1988.

Dunn, B. E. and Boone, M. A., "Growth of the Chick Embryo In Vitro", *Poultry Science*, 55:1067-1071 (1976).

Girard, H. and Visschedijk, A. H. J. "Altitude Hypocapnia at 2,800 m Does Not Affect Development of the Chicken Embryo", *Journal of Experimental Zoology Supplement*, 1:365-370 (1987).

Seymour, Roger S. and Piiper, Johannes, "Aeration of the Shell Membranes of Avian Eggs", *Respiration Physiology*, 71:101-116 (1988).

Ar, Amos and Rahn, Hermann, "Water in the Avian Egg: Overall Budget of Incubation", *Amer. Zoologist*, 20:373-384 (1980).

Romanoff, A. L. "Biochemistry of the Avian Embryo", *John Wiley and Sons*, New York, London, Sydney (1967).

Wittmann, J. et al., "Cultivation of the Early Quail Embro: Induction of Embryogenesis Under In Vitro Conditions", *Journal of Experimental Zoology Supplement*, 1:325-328 (1987).

Ar, A. et al., "The Avian Egg: Water Vapor Conductance, Shell Thickness, and Functional Pore Area", *Condor*, 76:153-158.

IN VITRO EMBRYO CULTURE TECHNIQUE

TECHNICAL FIELD

This invention relates to an in vitro avian embryo culture technique, which is particularly suitable for application to poultry, particularly hens.

BACKGROUND OF THE INVENTION

The chick embryo, in the initial stages of its development from fertilisation to cleavage, has not been amenable to experimental intervention on account of the bulk, fragility and relative inaccessibility of the ovum. This problem has been discussed in recent reviews on the possible routes of transfer of exogenous genes into birds (Freeman and Messer, 1985; Crittenden and Salter, 1986). Perry (1986a,b) has taken the alternative view and suggested that genetic manipulation of the avian ovum is practicable. The aim of devising a complete culture system for the chick embryo was to provide a means of rearing the manipulated ovum to maturity. A method has now been established for in vitro culture to an intermediate stage of embryonic development, and progress is being made on this account. The technique will have applications not only in the genetic engineering of poultry, but also in the investigation of fundamental mechanisms of avian development and in the study of deleterious traits. Moreover, it will afford a desirable alternative to surgical intervention in the laying hen.

The chick embryo originates in the germinal disc, a small region of cytoplasm situated at the animal pole of the ovum (the familiar yolk). During the first third of its development, the embryo remains floating at the surface of the yolk whilst the extra-embryonic membranes grow around the yolk and become vascularised. In the remaining period of development, the embryo grows at the expense of the food reserves in the egg. For present purposes, the development of the chick has been divided into 3 phases according to the changing requirements at successive stages from fertilisation to hatch.

Phase I. Fertilisation to blastoderm formation. This phase takes place in the oviduct and terminates at oviposition. Gamete interaction occurs within 15 min after ovulation, and the first cleavage division some 4 h later (Perry, 1987). In the following 20 h, subsequent divisions give rise to a simple sheet of cells overlying a subblastodermal cavity (Kochav, Ginsburg and Eyal-Giladi, 1980). During its passage through the oviduct, the ovum is invested with albumen in the magnum, then with the shell membrane in the isthmus where cleavage commences. In the uterus, the albumen is doubled in volume by the absorption of uterine fluid (pumping fluid), and finally the shell undergoes slow calcification. For hens laying in long sequences of one egg per day, oviposition is followed within 15-30 min by the next ovulation and the cycle is repeated.

Phase II. Embryonic morphogenesis. This phase takes place in the first 3 days of incubation of the egg (stages 1-18, Hamburger and Hamilton [1951]. At stage 20, the embryo is 10 mm in length, and the extra embryonic blastoderm extends around the yolk to its equator.

Phase III. Embryonic growth. This phase takes place in the final 18 days of incubation of the egg (stages 18-45, Hamburger and Hamilton [1951]).

Several methods are available for the short-term culture of embryos in Phase II (New, 1966) and for the long-term culture of more advanced embryos (Dunn, Fitzharris and Barnett, 1981; Ono and Wakasugi, 1984; Rowlett and Simkiss, 1985, 1987). Some involve transplantation of the embryo from the yolk, whereas others involve transfer of the embryo and intact yolk to a culture vessel. The latter method provides the more favourable conditions for long-term culture and is used exclusively for the present culture system.

SUMMARY OF THE INVENTION

The invention provides, in a first embodiment, a process for the in vitro culture of avian embryos during the embryonic growth phase, the process comprising incubating an embryo in a close container, there being an air space above the embryo, the air space being separated from the external atmosphere by a partially gas permeable seal. The container may be part of an egg, such as a hen egg, and the depth of the space between the embryo and the seal is preferably from about 5 to about 15 mm. The incubated embryo is preferably gently agitated, at least initially.

In a second embodiment, a process is provided for the in vitro culture of an avian embryo during embryonic morphogenesis, the process comprising incubating an embryo in a culture medium in a liquid-filled closed liquid-impermeable container. The container may be partially gas permeable, and the culture medium is preferably liquid albumen. The cultured embryos should be subjected to gentle to moderate agitation.

In a third embodiment, a process is provided for the in vitro culture of an avian embryo during embryonic morphogenesis and during the embryonic growth phase, the process comprising first culturing the embryo by a process in accordance with the second embodiment disclosed above and subsequently culturing the embryo by a process in accordance with the first embodiment disclosed above.

In a fourth embodiment, a process is provided for the in vitro culture of an avian embryo up to blastoderm formation, the process comprising culturing a fertilised ovum, having a surrounding capsule of dense albumen, partially submerged in culture medium. The medium should be generally in line with the germinal disc. A suitable culture medium is liquid albumen, which may be diluted by water and/or a salt solution. This process preferably takes place in a closed container.

In a fifth embodiment, a process is provided for the in vitro culture of an avian embryo up to blastoderm formation and during embryonic morphogeneiss, the process comprising culturing an avian embryo by a process in accordance with the fourth embodiment disclosed above and subsequently culturing the embryo by a process in accordance with the second embodiment disclosed above.

In a sixth embodiment, the invention provides a process for the in vitro culture of an avian embryo up to blastoderm formation, during embryonic morphogenesis and during embryonic growth to hatch, the process comprising culturing an avian embryo by a process in accordance with the fourth embodiment disclosed above, subsequently culturing the embryo by a process in accordance with the second embodiment disclosed above, and subsequently culturing the embryo by a process in accordance with the first embodiment described above.

BRIEF DESCRIPTION OF THE DRAWINGS

For a better understanding of the present invention, and to show how it may be put into effect, various embodiments will now be described, with reference to the following drawings, in which.

DETAILED DESCRIPTION OF THE PREFERRED EMBODIMENT

Figure 1:
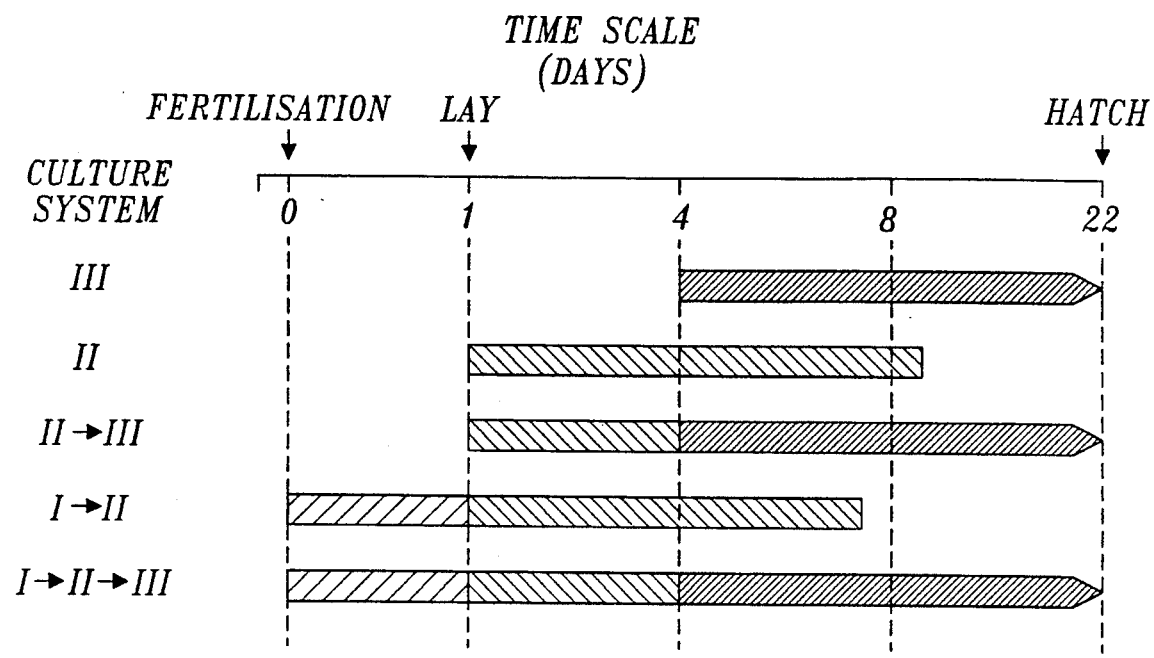
FIG. 1 shows a scheme of culture systems for chick embryos to indicate the periods of development covered by individual and linked systems, or a time scale of 0 to 22 days and specifically shows the period of chick embryonic development covered by a series of three culture systems, and the time of transfer of the embryos between systems for complete development in culture.

According to a first aspect of the present invention, there is provided a process for the in vitro culture of avian embryos during the embryonic growth phase, the process comprising incubating an embryo in a closed container, there being an air space above the embryo, the air space being separated from the external atmosphere by a partially gas permeable seal.

The seal is preferably in the form of a film. The seal may be of plastics material, for example polyethylene. It has been found that commercially available cling-film forms an appropriate seal, particularly when used in two layers. Any other material having the appropriate properties of cling film may be used.

The suitability of material for use as a seal may be measured indirectly by measuring carbon dioxide and/or water vapour permeability; carbon dioxide permeability can be measured by testing the rise in pH of egg albumen after 24 hours incubation at 38° C. in otherwise impermeable containers. The albumen should be initially gassed with carbon dioxide to lower the pH 0.1. A pH rise of from 0 5 to 1.5 is generally suitable, with the preferred range being 0.5 or 0.7 to 1.0 or 1.3, for example about 0.9. Water vapour permeability may be from 5 or 10 to 30 or 40 mg/cm$^2$/24 h.

The container is preferably part of an egg, which will usually be chosen from the same species as is being cultured. It has been found particularly appropriate to remove the blunt end from a whole egg; a 40 mm diameter hole centered on the axis of the egg was found to be particularly suitable.

The hole at the blunt end of the egg is sealed with the partially gas permeable seal. The seal may be made to adhere to the egg shell by means of albumen. Preferably the permeability characteristics are similar to those of a natural egg.

Culture medium may be present in some embodiments of this aspect of the invention, particularly if prior culture stages have been in vitro, but the process can work without it, for example when the prior culture stages have been carried out naturally. The culture medium when present will usually comprise albumen, either undiluted or in a dilute form and desirable interuterine fluid.

When hen eggs are used, it is preferred that the depth of the space between the embryo and the seal is from 5 to 15 mm, for example about 10 mm.

It is preferred to agitate the incubated embryo gently, at least initially. Gentle agitation can be achieved by intermittent rocking, for example through an angle at 30°. Conventional incubation temperatures, for example about 38° C. may be maintained.

In vitro culture processes in accordance with this aspect of the invention are suitable for use from about day 4 (counting from fertilisation) up to hatch, which generally occurs at about day 22. However, for the final few days (for example 13) of embryonic life, it is preferred that there be no agitation. In addition, shortly before (for example 1 to 2 days before) the estimated hatch time it is preferred that the seal be perforated to allow a certain amount of air into the container. Further air may be allowed in later, for example by removing the seal and optionally covering the hole in the eggshell (when the egg forms the container) by a solid disc, which may be provided by a petri dish.

According to a second aspect of the present invention, there is provided a process for the in vitro culture of an avian embryo during embryonic morphogenesis, the process comprising incubating an embryo in a culture medium in a liquid-filled closed liquid-impermeable container.

The container may be partially gas permeable. The gas permeability may be provided by an eggshell (generally in combination with the inner shell membrane) and/or by an otherwise partially gas permeable seal, whose preferred characteristics are as for the first aspect of the invention. It should be noted that the eggshell and inner shell membrane are partially gas permeable.

The culture medium is preferably liquid albumen, which may be collected from freshly laid eggs.

The container is for preference again part of an egg, but the preferred construction is somewhat different from that of the first aspect of the invention. In the present aspect, it is preferably the sharp end which is removed, for example by a 32 mm hole. This ensures the presence of an air space between the outer shell membrane and the inner shell membrane; this appears to be advantageous as the air space expands during culturing to make up for the water lost by evaporation.

If a seal is being used to close an egg of which the sharp end has been removed, the egg may be cultured in a generally horizontal position, with the seal then being to one side. The seal should be kept firmly in place against the shell of the egg.

It is very much preferred that the cultured embryos be subjected to gentle to moderate agitation. Intermittent or continuous rocking, for example through an angle of 90° in hourly cycles, or other comparable intervals, is preferred.

A process in accordance with this aspect of the invention will generally begin at about 1 day after fertilisation (that is to say about the normal time of laying) and may last for 2 or more days, for example up to 8. However, it is preferred that a process in accordance with this aspect of the invention only be continued for in the order of 3 or 4 days before transferring the embryo to a process in accordance with the first aspect.

According to a third aspect of the present invention there is therefore provided a process for the in vitro culture of an avian embryo during embryonic morphogenesis and during the embryonic growth phase, the process comprising first culturing the embryo by a process in accordance with the second aspect of the invention and subsequently culturing the embryo by a process in accordance with the first aspect.

It is preferred that the transition occurs between 2 and 5, for example 4, days after fertilisation.

According to a fourth aspect of the present invention, there is provided a process for the in vitro culture of an avian embryo up to blastoderm formation, the process comprising culturing a fertilised ovum, having a surrounding capsule of dense albumen, partially submerged in culture medium. For optimal results, the medium should be generally in line with the germinal disc, which will generally be uppermost, but below the level of the albumen capsule.

The fertilized egg may be obtained surgically from the hen. If surgical techniques are used, the egg is preferably taken from the mid magnum, for example from 50 to 150 mm from the isthmus. Taking a fertilized egg from this area of the magnum has been found to be advantageous in that the fertilized ovum then appears to have an optimum thickness of the surrounding capsule of dense albumen.

The culture medium can be liquid albumen which may be diluted by water and/or a salt solution. It is generally preferred to initiate culture with dilute albumen (for example 3:2) with salt solution and subsequently (for example after 1 day) to dilute the albumen with salt solution (for example 2:1).

A process in accordance with this aspect of the invention preferably takes place in a closed container. The container may be made of an impermeable material such as glass, which may be sealed with a low gas permeability film such as SARAN WRAP (trade mark). Any other material having the appropriate properties of SARAN WRAP may be used. Gas permeability may be measured (eg for carbon dioxide and/or water vapour) as described above. The 24 hour pH rise may be from 0.5 to 1.0, for example from 0.6 to 0.8 in the carbon dioxide permeability test. The water vapour permeability may be from 1.0 to 10, for example 2 to 5 mg/cm$^{2/24}$ h.

It will generally be the case that an embryo cultured in accordance with this aspect of the invention will subsequently be cultured in accordance with a process of the second aspect of the invention. Therefore, according to a fifth aspect of the invention, there is provided a process for the in vitro culture of an avian embryo up to blastoderm formation and during embryonic morphogenesis, the process comprising culturing an avian embryo by means of a process in accordance with the fourth aspect of the invention and subsequently culturing the embryo by a process in accordance with the second aspect.

If it is desired to use a practically complete culture system for avian embryos from fertilized ovum to hatch, it will be understood that it is appropriate to adopt various of the above aspects of the invention in sequence. Therefore, according to a sixth aspect of the present invention, there is provided a process for the in vitro culture of an avian embryo up to blastoderm formation, during embryonic morphogenesis and during embryonic growth to hatch, the process comprising culturing an avian embryo by a process in accordance with the fourth aspect of the present invention, subsequently culturing the embryo by a process in accordance with the second aspect of the culturing invention and subsequently the embryo by a process in accordance with the first aspect of the invention.

It will generally be preferred that the recipient eggs, if eggs are used as containers, in the second stage are slightly larger than the donor eggs, for example by an amount of to 2 ml. If eggs are used as the containers in the third stage, the recipient eggs are preferably substantially (for example about 18 ml) larger than that used in the immediately preceding stage.

Various examples of the invention will now be given. In the examples, the following materials are used, unless otherwise stated.

The survival rates of cultured embryos are summarised in Table 1.

TABLE 1

Survival rates of chick embryos grown for specified periods in culture systems appropriate for particular phases of development from 2 h post-fetilisation (day 0)

| Period of development | Culture systems | No. of embryos cultured | No. of surviving embryos or chicks (%) |
|---|---|---|---|
| Day 4 to hatch | III | 69 | 25 (36) |
| Day 1 to day 8 | II | 47 | 35 (74) |
| Day 1 to hatch | II to III | 59 | 16 (27) |
| Day 0 to day 7 | I to II | 35 | 23 (67) |
| Day 0 to hatch | I to II to III | 96 | 8 (8) |

Animals. Laying hens of a commercial strain of Warrens (Isa Brown) were housed in individual cages and maintained on a 14 h light/24 h cycle. At 28–32 weeks of age, when laying in long sequences of 1 egg/day, they were artificially inseminated with freshly collected semen from Rhode Island Red cockerels.

Fertility was regularly checked by visual inspection of unincubated eggs and found to be better than 90%. In fertile eggs, the germinal region is seen as a white ring (3–4 mm in diameter) enclosing a semi-transparent area, and in infertile eggs it appears as a vacuoloated disc (2–3 mm in diameter).

Figure 2:
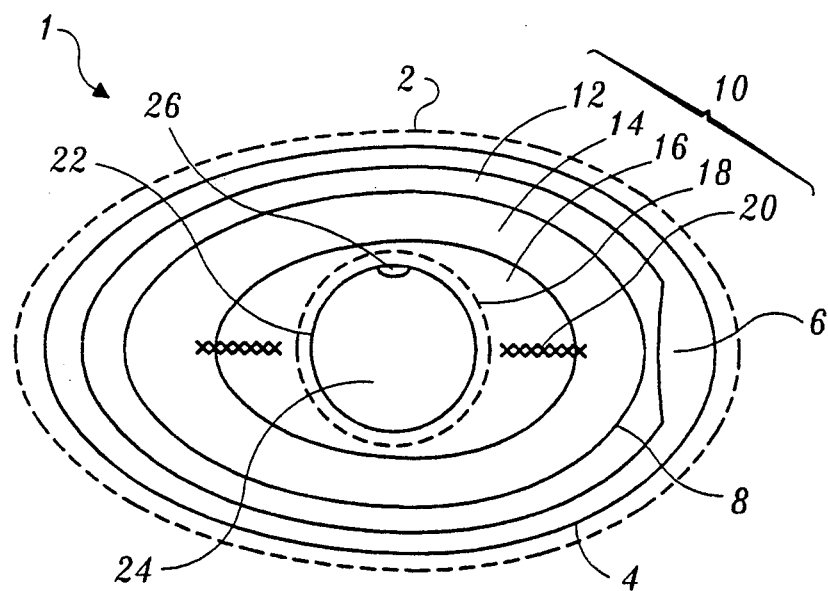
FIG. 2 (prior art) illustrates the structure of the newly laid egg of the hen.

Eggs. Eggs laid in the preceding 24 h by the laying stock were used as a source of embryos for culture systems II and III (Examples 1–3). Freshly laid eggs (fertile and infertile) from this stock were also used as a source of albumen for the culture medium. Liquid albumen was collected from the inner and outer albumen layers of the egg (FIG. 2) and used within the same day for culturing. Recipient shells for culture system II (Examples 2–5) were obtained from the laying stock. The larger shells used as culture vessels for system III (Examples 1, 3, 5) were from double-yolked eggs of a commercial broiler strain obtained from a local hatchery (D.B. Marshall, Whitburn, West Lothian) and used for culture within 1–2 weeks of lay.

Wrapping Film. Two kinds of plastic wrap were employed for sealing the culture vessels. SARAN WRAP (Dow Chemical Company) has low gaseous permeability (Dunn, Fitzharris & Barnett, 1981) and was most suitable for system I. Cling film (any brand except for preference those lacking PVC additives) is partially permeable to gases (Dunn et al. 1981) and was used for systems II and III. Permeability tests were made on the wrapping films presently employed in the conditions used for incubating the cultured embryos. Permeability to $CO_2$ was determined indirectly by measuring the rise in pH of culture medium (liquid albumen:salt solution, 2:1) in glass jars (60 ml; diameter, 40 mm) containing 25 ml of medium and sealed with wrapping film. The culture medium was initially gassed with $CO_2$ to lower the pH to an appropriate value. For SARAN WRAP (one layer), the pH rose by an average of 0.7 unit, from pH 7.2–7.5 to pH 7.8–8.2, during incubation for 24 h at 41.5° C. and zero humidity. For cling film (2 layers), the pH rose by an average of 1.0 unit, from pH 7.2-7.5 to pH 8.3-8.5, during incubation for 24 h at 38° C. and R.H. 45-55%. Permeability to water vapour was determined by measuring the water loss from dishes (350 ml; diameter, 104 mm) containing 150 ml water. The dishes were sealed with wrapping film and incubated as described previously. For SARAN WRAP, the average permeability was 3.4 mg/cm$^2$/24 hr (range, 3.203.8 mg). For cling film, the average permeability was 22 mg/cm$^2$/24 hr (range, 15-28 mg).

Incubation. A number of forced air, cabinet model incubators with automatic turning mechanisms (CURFEW Model 248) were employed for culturing the embryos. The conditions of temperature, humidity and angle of tilt of the trays in each incubator were adjusted to meet the requirements at particular periods of embryonic development. Cultures were transferred from one incubator to the next at appropriate times and inspected at intervals of no less than 2 or 3 days. For the pre- and immediate post-hatch period, the cultures were placed in a table-top, still air incubator (CURFEW Model 146) fitted with a transparent lid to allow frequent inspection. The humidity was maintained at a given level, measured with Fischer hair hygrometers (Gallenkamp), using dishes (2 liter capacity) of water placed on the bottom of the incubators. The machines were cleaned and disinfected monthly with MILTON sterilising fluid (Richardson-Vicks Ltd). Sterility. All operations were conducted in semi-sterile conditions. The bacteriostatic properties of egg albumen made it unnecessary to take stringent aseptic precautions. Eggs were briefly rinsed in 70% alcohol shortly after collection, and then swabbed with 70% alcohol immediately before use. All equipment, distilled water and saline solutions were autoclaved. The salt solutions were filter sterilised. For the wrapping film, the outer layers of the roll of film were discarded, then sheets (100 mm$^2$) were cut and placed between sheets of sterile paper. This operation, collection of egg albumen and preparation of the cultures were performed in clean air cabinets. Antibiotics (penicillin, 100 u/ml; streptomycin, 100 mcg/ml) were added to the egg albumen which was used to glue the cling film closure to the recipient shells in system III.

EXAMPLE 1

Figure 3:
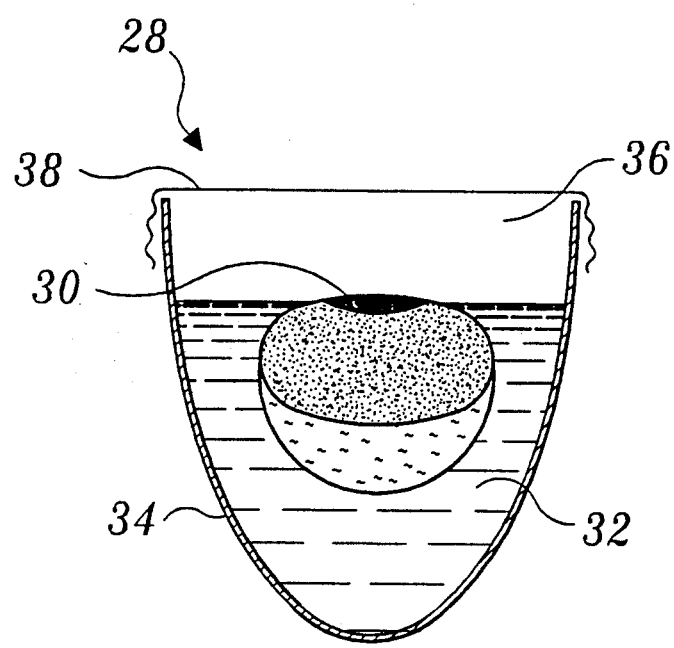
FIG. 3 is a diagram of a culture system for Phase III (day 4 to hatch)

Culture of embryos from day 4 of development to hatch. Culture system III Method Recipient shells were prepared from double-yolked eggs. A circle of 40 mm in diameter was drilled around the blunt end of the egg and the cap of the shell, containing the air cell, was removed. After discarding the contents, the shell was rinsed out with distilled water, then refilled with water to prevent dehydration of the inner shell membrane. The volumes of the recipient shells ranged from 65 to 75 ml. Three-day incubated eggs, containing embryos at stages 15-20, were cracked open and the contents lowered into a shallow dish lined with cling film. The embryos were transferred in the cling film sac to the recipient shells, then the cling film was slowly withdrawn, keeping the embryos uppermost. Details of the transfer method are illustrated in a report by Rowlett and Simkiss (1987). The shell was sealed with 2 layers of cling film, using liquid albumen to glue the film to the shell (FIG. 3). The depth of the space between the embryo and the film was 10 mm on average.

The cultures were incubated at 38° C. and rocked intermittently through an angle of 30° for 5 days, then they were maintained in a stationary position for 10 days. For the final 3-4 days, they were placed in a stationary hatching incubator at 37° C. The relative humidity ranged from 45-60%. At 1-2 days before the estimated time of hatch, when the beak had pipped the chorioalloantoic membrane and penetrated the air space, small perforations were made in the cling film. The cling film was replaced with a petri dish lid several hours before hatch.

The hatch rate was 36% (Table 2), and 72% of the hatchings appeared healthy. Their average weight was 35 g as compared with 46 g for control chicks grown in ovo. Abnormalities of the weaklings included incompletely retracted yolk sacs, unhealed navels and limb defects. Sticky chicks were common, the condition being associated with the presence of some unabsorbed albumen in the shell.

TABLE 2

Survival rates of chick embryos at intervals after transfer to recipient shells on the third day of incubation in ovo. Culture system III.

| Days of incubation from lay | Number of live embryos | Live embryos/ total cultures (%) |
|---|---|---|
| 3 | 69 | |
| 9 | 48 | 69 |
| 14 | 39 | 57 |
| 18 | 32 | 46 |
| 21 | 27 | 39 |
| Hatched 21-22 | 25+ | 36 |

+The number of hatched chicks includes healthy chicks and weaklings

Ono and Wakasugi (1984) devised a shell technique for culturing quail embryos obtained from 3-day incubated eggs; they demonstrated that the egg shell was an essential source of calcium for the embryo. Rowlett and Simkiss (1985, 1987) adapted the technique for the domestic fowl and obtained a hatch rate of 20%. It seems that the function of the chorioallantoic membrane in calcium absorption and gas exchange was not impaired by strain or species differences between donor embryo and host shell.

Rotation of the cultures during the first part of incubation has been recommended by Rowlett and Simkiss (1987). Though it is common practice to rotate hens' eggs throughout incubation, New (1957) showed that the critical period is during the third to the eighth day of incubation. In a series of trials, it has now been confirmed that turning the cultures is a requirement for optimum development and shown that this movement need only be imposed during the first 5 days of incubation of the cultures (days 4-9 of development) In our experience, unturned cultures gave a hatch rate of 18% (n=77) as compared with a rate of 36% (Table 2) for cultures that were rotated for 5 days and then maintained in a stationary position. Extending the period of rotation to 15 days resulted in poorer hatchability. The hatch rates, as a percentage of live embryos on day 9 of development, were 62% (n=33) for the cultures rotated for the first 5 days only, and 40% (n=71) for the cultures rotated for 15 days.

Cling film seals for the recipient shells were used in place of the loose fitting lids employed by other workers. An advantage of this modification is that standard conditions of incubation for eggs (a forced air system, R.H. 50-60%) can be employed, so that the region of the chorioallantoic membrane associated with the recipient shell is subject to a normal environment. At high humidity, greater than R.H. 70%, the hatch rate was reduced to 10% (n=38). The cling film may be effective in regulating the environment in the space above the embryo by restricting gas exchange and water loss from this compartment. In the air cell of the egg, the water vapour pressure is higher than ambient and the $O_2$ tension falls as the $CO_2$ tension rises with time of incubation (Wangensteen and Rahn, 1970/71). Wrapping films which are partially permeable to gases have been shown to provide optimum conditions for the development of chick embryos in shell-less culture (Dunn et al., 1981). In experiments with unsealed shells, cultures have been incubated at high humidity, in 1.5% $CO_2$ for quails (Ono and Wakasugi, 1984) and in air for chicks (Rowlett and Simkiss, 1987). The latter investigation suggests that the maintenance, in the culture vessel, of an $O_2/CO_2$ differential with air is less important for normal development in culture than is the prevention of water loss from the unprotected chorioallantoic membrane facing the air space. In the present example, a double layer of cling film was employed as in some circumstances few embryos survived to day 19 in shells sealed with a single layer of film. A second advantage of cling film is that it may help to reduce contamination by microorganisms.

EXAMPLE 2

Culture of embryos from day 1 to day 9 of development. Culture system II Method

Figure 4:
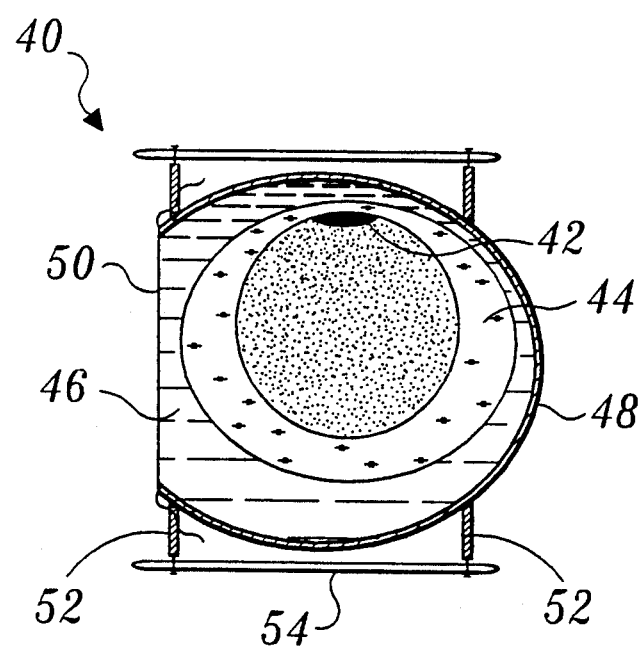
FIG. 4 is a diagram of a culture system for Phase II (day 1 to day 4 or day 9)

Eggs that were 3-4 g heavier than the donor eggs were selected for recipient shells. An aperture, 32 mm in diameter, was drilled in the sharp end of the shell, and the contents discarded. The shells were rinsed out with distilled water, then refilled with water to prevent dehydration of the inner shell membrane. An incision was made with scissors in the shell of an unincubated, fertile egg, the shell cracked open by hand and the contents lowered into a glass jar (diameter, 50 mm; volume, 60 ml). They were then transferred to a recipient shell via a beaker (diameter, 35 mm; volume, 70 ml). This procedure ensured minimal damage to the blastoderm, yolk and capsule of viscous albumen. The shells were filled to the brim with liquid albumen (1-5 ml) collected from freshly laid eggs, and the aperture sealed with a sheet of cling film, taking care to avoid the inclusion of air bubbles in the preparation. The cling film was held in position by 2 rings (nylon) placed over either end of the shell and secured by elastic bands hooked 0 over a set of small pegs (FIG. 4). The reconstituted eggs were incubated on their sides, and rocked, intermittently or continuously, through an angle of 90° hourly cycles at 38° C. and relative humidity of 30-50%. The cultures were candled at 7, 9 and 10 days of incubation, and the surviving embryo reincubated. Embryos showing normal development were observed in 74% of the cultures at 7 days of incubation (Table 3). Mortality was high in the following 2 days and only 1 embryo survived beyond the tenth day. In all preparations the air cell at the blunt end of the shell had expanded to replace the water lost by evaporation.

TABLE 3

Survival rates of chick embryos at intervals after transfer from unincubated eggs to recipient shells. Culture system II

| Days of incubation from lay | Number of live embryos | Live embryos/ total cultures (%) |
| --- | --- | --- |
| 0 | 47 | |
| 6 | 39 | 83 |
| 7 | 35 | 74 |
| 9 | 15 | 32 |

Callebaut (1983) has described a method for the culture of quail embryos in recipient egg shells for 2-3 days (data were not given). The technique consisted of transferring the contents of a fertile donor egg to an empty host shell, then sealing the preparation with a petri dish and molten paraffin wax. For chick embryos, the method has been refined by using cling film as a seal and rotating the preparations during incubation. In experiments on stationary cultures the survival rate was 50% at 7 days and these embryos were usually retarded in developmental age. In attempts to rear day 1 embryos in culture systems I and III that contained an air space, it was found that mortality was high during the second to the third day of incubation. Similar observations have been made by Dunn et al. (1981) in their shell-less culture systems. Developmental failure in these systems can perhaps be attributed to the fact that the blastoderm is covered by only a thin layer of albumen. Romanoff (1943) has emphasised the importance of submersion in liquid albumen for the development of the blastoderm on whole yolk. The continuous bathing of the blastoderm region with liquid albumen, a condition obtained in a shell from which air is excluded, may aid in the formation of the sub-blastodermal cavity. This cavity becomes filled with fluid, derived from the albumen, during early development (New, 1956). Presumably the process is impaired in preparations lacking sufficient quantities of albumen in the vicinity of the embryo.

Callebaut's (1983) culture system for quail embryos has been modified in this Example by, among other things, substituting cling film for the petri dish/paraffin wax seal, by rotating the cultures during incubation and by adapting it for chick embryos. The modifications extended development in culture by 4 days and resulted in a high survival rate.

EXAMPLE 3

Culture of embryos from day 1 of development to hatch. Culture systems II to III Method Embryos from unincubated eggs were cultured for 3 days as described in Example 2 (FIG. 4). The preparations were then removed from the incubator, one at a time, an incision made in the shell and the contents transferred to a larger shell as described in Example 1 (FIG. 3) Attempts to remove the contents of the smaller shell through the existing aperture invariably damaged the embryo and the extra-embryonic membranes. The cultures were incubated as described in Example 1.

The survival rates are given in Table 4.

TABLE 4

Survival rates of chick embryos at intervals after transfer from unincubated eggs to small recipient shells, and after 3 days, to large recipient shells. Culture systems II to III.

| Days of incubation from lay | Number of live embryos | Live embryos/ total cultures (%) |
|---|---|---|
| 0 | 59 | |
| 3 | 55 | 93 |
| 9 | 34 | 58 |
| 14 | 28 | 47 |
| 18 | 21 | 36 |
| 21 | 17 | 29 |
| Hatched 21-22 | 16+ | 27 |

+The number of hatched chicks includes healthy birds and weaklings

The losses in the early part of incubation were compounded of embryos that failed to develop in system II and embryos that were damaged during transfer to system III. Mortality between the third and ninth day was probably also due to damage during transfer. The hatch rate was 27% and, as described in Example about 20% of the hatchlings displayed leg and yolk sac defects. Some neonates were reared to maturity and tested for viability of the gametes. The hatch rate of eggs from 2 experimental hens (egg production rates of 89% and 75% respectively), artificially inseminated from Rhode Island Red cockerels, were 63% and 80%, respectively. The hatch rates of eggs from Warren hens, artificially inseminated from 2 experimental cockerels, were 80% and 15%, respectively. Two experimental hens did not come in to lay.

In culture system II, developmental arrest occurred at days 8-10 of development and appeared to be associated with a lack of contact between the chorioallantoic membrane and the inner shell membrane The disruption of the chalaza in the reconstituted egg may have affected the buoyancy of the yolk and, in turn, the distance of the extra-embryonic membranes from the shell membrane, thereby impairing the mechanism for gaseous exchange. To circumvent this problem, the embryos were transferred to a system in which the vascular extra-embryonic membranes were in proximity with the air/albumen interface. The most suitable time for the transfer to culture system III was towards the end of the third day of incubation when the development of the vasculature was underway and the components of the reconstituted egg were still sufficiently robust to withstand handling. Certain experiments in which embryos were cultured from day 1 of development in stationary shells containing an air space (FIG. 3), gave low survival rates and zero hatchability (M. Naito, personal communication). The step linking the Phase II to the Phase III system is a new procedure. This is the first report of the successful culture of avian embryos from the blastoderm stage (Stage 1) to hatching.

EXAMPLE 4

Culture of fertilised ova to day 7. Culture systems I to II. Method

Hens were taken at 2.75 h after the estimated time of lay, having ascertained that the laid egg was fertile. At this time in the daily reproductive cycle the next ovum has ovulated and is traversing the magnum where the albumen is deposited. For recovery of the oviductal embryos, the hens were killed with an intravenous injection of sodium pentobarbitone (EXPIRAL, Ceva Ltd.), the abdomen was plucked and swabbed with 70% alcohol. The portion of the oviduct containing the fertilised ovum was lifted out of the abdominal cavity and, after excision, it was placed in a sterile basin containing paper moistened with saline. Most of the ova were located at a distance of 50-150 mm from the border of the magnum with the isthmus.

Figure 5:
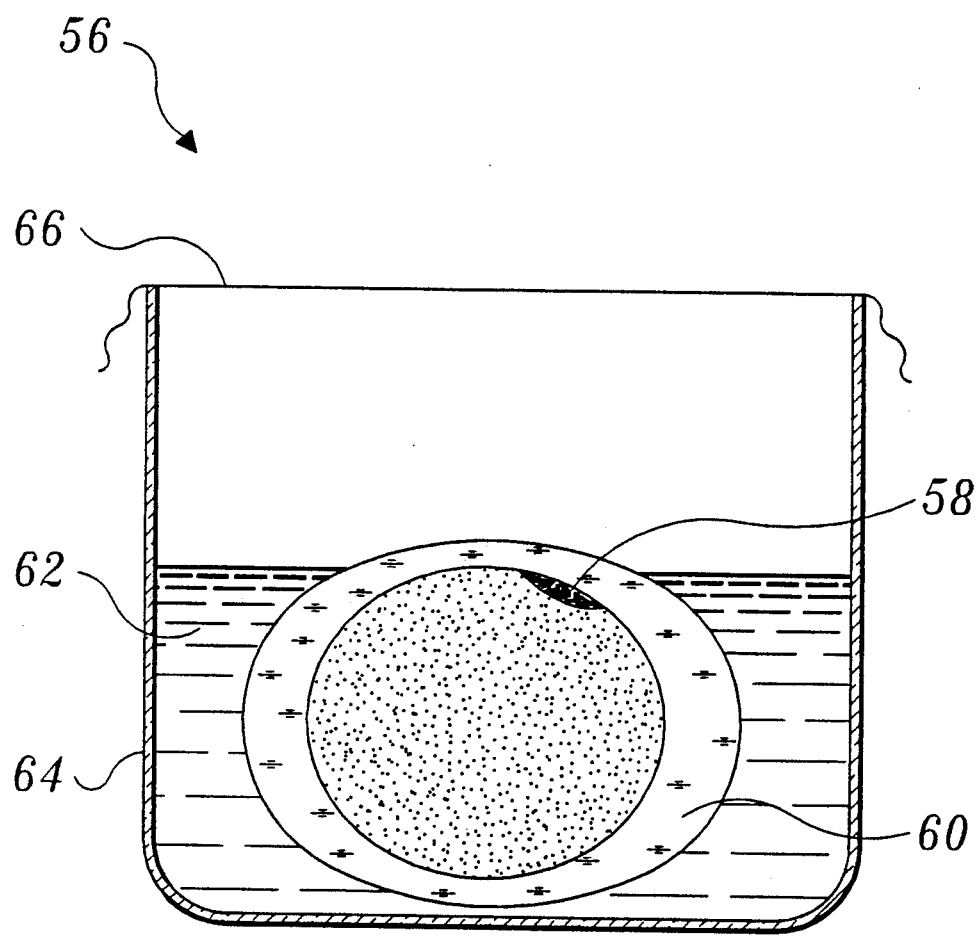
FIG. 5 is a diagram of a culture system for Phase I (fertilised ovum to day 1).

A long incision was made in the oviduct wall and the ovum slid into a glass beaker (diameter, 35 mm; volume, 70 ml), avoiding damage to the capsule of viscous albumen around the yolk. The ova were transferred to glass jars (diameter, 40 mm, volume, 60 ml) containing about 5 ml of culture medium, and the yolk was manoeuvered to bring the germinal disc uppermost. Medium was added to a level in line with the germinal disc, but below the surface of the albumen capsule, and the container sealed with SARAN WRAP secured with an elastic band (FIG. 5). The total volume of medium required depended on the size of the yolk plus albumen capsule and amounted to 8-12 ml. For cultures in which the germinal disc lay to the side of the yolk, the containers were tilted to ensure that the albumen capsule above the germinal disc was not submerged in medium. The preparations were incubated at 41°-42° C. for 24 h, with a delay of no more than 20 min between retrieval of the ovum from the magnum and incubation.

The culture medium consisted of liquid albumen (2 parts), collected from the inner and outer albumen layers of freshly laid eggs, and salt solution part) The salt solution contained 50mM $KHCO_3$, 30 mM $NaHCO_3$, 10 mM KCl, 2.5 mM $MgCl_2.6H_2O$, 0.7mM $CaCl_2.2H_2O$ and 11 mM glucose. The pH of the culture medium was lowered from an initial value of 8.4 to 7.2-7.4 by stirring in an atmosphere of $CO_2$, and was maintained at the lower value during the course of the preparative procedures by storing the medium in sealed containers.

The state of development after 24 h can be roughly ascertained by visual inspection of the germinal area. Growth of a blastoderm and formation of a subblastodermal cavity is indicated by an opaque ring (3 mm in diameter) enclosing a semi-transparent area However, for an accura.te assessment of developmental potential, the preparations were cultured for a further 3-6 days in system II.

Embryos were placed in the culture system for Phase II as described in Example 2. Recipient shells were prepared from eggs that were about 3-4 g heavier than the preceding eggs laid by the donor hens. The cultures were cooled to ambient temperature and placed in the recipient shells which were then filled with the culture medium (10-20 ml) and sealed with cling film (FIG. 4). The reconstituted eggs were incubated on their sides at 38° C., R.H.30-50%, with intermittent rocking through an angle of 90° in hourly cycles. The cultures were removed from the shells for examination at 7, 8 or 9 days of incubation.

The results are given in Table 5.

TABLE 5

Development of fertilised chick ova recovered from the magnum at 2.75 h after the preceding eggs were laid. Culture systems I to II.

| Number of ova | Number of embryos at Stages 27-29 | Viability of embryos on given days of incubation | | |
|---|---|---|---|---|
| | | 7 | 8 | 9 |
| 35 | 24 | 2/2 | 9/17 | 0/4 |

Normal embryos developed to stages 27-29 in 67% of the cultures. They did not survive beyond this stage, usually dying early in the eighth day of incubation. In the remaining cultures there was either no development, or development of a blastodermal sheet of cells only, or a malformed embryo (see Tables 6, 7).

TABLE 6

Development of fertilised chick ova cultured in recipient shells (system II) throughout incubation. Phase I culture system trial+.

| Number of ova | Incubation (days) | Percentage of cultures | | | |
|---|---|---|---|---|---|
| | | Viable embryos* | Malformed embryos | Blastodermal growth | Germinal discs |
| 48 | 3–5 | 19 | 6 | 46 | 29 |

+For the first 24 h, the reconstituted eggs were placed in sealed plastic bags and rocked through an angle of 90° in hourly cycles. Thereafter they were incubated by the method for system II.
*The embryos were retarded in developmental age by 12 h or more

TABLE 7

Development of fertilised chick ova in culture media consisting of liquid albumen, undiluted, or diluted with salt solution or water alone. Phase I to II culture system trials.

| Medium | Number of ova | Incubation (days) | Percentage of cultures | | | |
|---|---|---|---|---|---|---|
| | | | Normal embryos+ | Malformed embryos | Blastodermal growth | Germinal discs |
| Undiluted | 35* | 6–7 | 51 | 17 | 29 | 3 |
| Diluted: | | | | | | |
| salt solution | 90* | 7–8 | 51 | 13 | 24 | 12 |
| water | 17 | 7–8 | 59 | 18 | 0 | 23 |

+Mortality was high at 7 days' incubation in undiluted albumen, and 8 days' incubation in diluted albumen.
*In these preparations, the culture vessels for the Phase I system were sealed with cling film and a layer of cling film was placed directly over the albumen capsule The culture system for Phase I was based on a series of experiments designed to test the requirements for the first 24 h of development. Tests were made on ova at different stages after fertilisation and subjected to different treatments, before transfer to the standard culture system for Phase II for further development and analysis. Aspects of the culture system that were examined were: the depth of material overlying the germinal disc, the composition of the culture medium, gaseous exchange and the spatial position of the germinal disc.

An important factor was the depth of albumen above the germinal disc. Ova encased in relatively thin albumen capsules, from the anterior magnum, or in thick albumen capsules from the posterior magnum, gave lower survival rates than ova retrieved from the mid-magnum (50–150 mm from the isthmus). Development of ova from the mid-magnum was arrested if the albumen capsule was removed, allowing the germinal disc to float to the surface of the medium. Development was also arrested if the ovum, complete with capsule, was submerged in medium. In experiments (Table 6) on the use of system II (FIG. 4) for the culture of fertilised ova, the most likely cause of developmental failure was submersion of the encapsulated ovum in culture medium. In such preparations, incubated with the sealed surface uppermost for the first 24 h, the distance of the germinal disc from the cling film seal varied, and depended on the buoyancy of the yolk.

A precisely defined culture medium was not essential for development in Phase I. Embryos grew well in undiluted albumen for 6 days to Stages 25-26. However, for development beyond this stage it was necessary to use diluted albumen (Table 7). The composition of the salt solution was based on data given by Beadle, Conrad and Scott (1938) and Leonard (1968) for differences in ionic composition of the albumen of uterine eggs, prior to plumping, and of the albumen of laid eggs.

Glucose was added at a concentration equivalent to that in uterine fluid (Davidson and Draper, 1969) at the commencement of the uterine phase of egg formation. In the reconstituted eggs, the total amount of fluid (salt solution plus plumping fluid) was roughly similar to the amount of plumping fluid in the laid egg. Plumping fluid comprises about half of the albumen content of the egg, which varies from 36 to 40 ml between eggs. Experiments in which the albumen in the medium was diluted solely with distilled water gave similar results to those obtained using salt solution as a diluent (Table 7). Thus, for short-term culture to Stage 29, water is an important ingredient.

The gaseous environment in the culture vessel and the related acid-base balance of the medium did not require precise adjustment for development in the oviductal phase. In utero, the pH of the albumen fluctuates between 7.15 and 7.4 (Sauveur and Mongin, 1971). In the egg, it rises to pH 8.4 within a few hours of lay, due to the efflux of $CO_2$ through the shell (Dawes, 1975). Conversely, the oxygen content of the albumen in utero is low, and in the egg it equilibrates with air within 2 h of incubation (Wishart, personal communication). For the definitive culture method for Phase I, the pH of the medium was routinely adjusted to 7.2–7.4, with $CO_2$ to conform with the in vivo conditions; the oxygen level of the medium was assumed to be ambient. The vessels were sealed with WRAP to maintain the pH below 7.8, and to maintain humid atmosphere in the chamber.

Development was not impaired by culture at a higher pH though there was a slight reduction in the number of surviving embryos. Fertilised ova were placed in recipient shells, filled with medium, pH 7.4 to a level in line with the germinal disc and the shells covered with lids. They were incubated in 10% $CO_2$, or in air, R.H. 80%, at 42° C. for 24 H. The pH of the culture medium rose by an average of 0.31 units and 1.15 units, respectively. The embryos were then cultured in system II for a further 6 days. Normal embryos developed in 55% (n=33) of cultures incubated in 10% $CO_2$, and in 41% (n=29) of cultures incubated in air.

It has been proposed that determination of bilateral symmetry in the uterine phase of development is influenced by gravity (Kochav and Eyal-Giladi, 1971). Experiments on the spatial position of the germinal area have indicated that embryonic axes are formed in embryos placed obliquely, and not in those placed horizontally, during the critical period for determination (Olzanska, Sjolajska and Lassota, 1984). In the present work no evidence was obtained to support these findings. Embryonic axes were formed in 68% (n=34) of cultures grown from horizontal germinal discs and in 74% (n=34) of cultures grown from oblique germinal discs.

The method for Phase I and its linkage with the method for phase II is entirely new. This is the first report of the growth in vitro of avian embryos from fertilised ovum to Stage 29 i.e. for a period covering the first third of the embryonic life-span. There are two other reports on the culture of oviductal embryos on whole yolk. Howarth (1971) has cultured ova, obtained from the anterior region of the oviduct, to the blastoderm stage (St. 1) with a survival rate of 60%, (n=10). To prevent the yolk from floating to the surface, the ova, which at this stage lack an albumen capsule, were placed in plastic shells immersed in beakers of liquid albumen. Kochav and Eyal-Giladi (1971) have grown uterine embryos from the multicellular stage to the 4-somite stage (St. 8). In this study, the shell membrane was removed, the yolk and albumen transferred to a beaker of physiological salt solution, and the yolk suspended by the chalaza to force the germinal area into a oblique position.

The culture method for the development of the fertilised ovum for a period of 7 days provides a model system for testing the effects of experimental intervention at precleavage stages on a range of developmental processes in birds. In this laboratory, we have injected exogenous genes into the cytoplasm of the germinal disc and examined their fate in the embryos at intervals from 2 h to 7 days.

EXAMPLE 5

Culture of fertilised ova to hatch. Culture systems I to II to III Method

Ova recovered from the mid-magnum region of the oviduct were cultured for 24 h in the system for Phase I (FIG. 5), transferred to the system for Phase II (FIG. 4) and incubated for 3 days. The procedures are described in Example 4, with the modification that the proportions of liquid albumen to salt solution in the culture medium were 3:2 for system I and 2:1 for system II. In order to ensure that the requisite amount of culture medium was supplied to the embryo for its long-term development, the recipient shells prepared for system II were 1-2 ml larger in volume than those of the preceding eggs laid by the donor hens. After a total of 4 days, incubation, the embryos were transferred to the system for Phase III (FIG. 3) as described in Example 3. The recipient shells prepared for system III were, on average, 18 ml larger in volume than the recipient shells used in system II. The volume difference determined the size of the airspace in the chamber. The cultures were incubated at 38° C. for 5 days, turning them through an angle of 30°, then for 10 days in a stationary position, and finally placed in a stationary hatching incubator at 36-37° C. (Table 8).

TABLE 8

Procedure for incubation of chick embryos from fertilised ovum to hatch

| Successive days of incubation | Rocked/ stationary | Angle | Temperature (°C.) | Relative humidity (%) in incubator |
|---|---|---|---|---|
| 0-1 | Stationary | — | 41-42 | 0 |
| 1-4 | Rocked | 90° | 38 | 30-50 |
| 4-9 | Rocked | 30° | 38 | 30-50 |
| 9-19 | Stationary | — | 38 | 40-55 |
| 19-22 | Stationary | — | 36-37 | 40-60 |

The results of 9 experiments in which the cultures were incubated from the fourth to the nineteenth day at relative humidity, R.H. 30-55%, are given in Table 9.

TABLE 9

Survival and hatch rates of fertilised chick ova at intervals in culture. Culture systems I to II to III.

| Days of incubation | Number of live embryos | Live embryos/ total cultures (%) |
|---|---|---|
| 0 | 96 | |
| 4 | 55 | 57 |
| 10 | 31 | 32 |
| 15 | 26 | 27 |
| 19 | 18 | 19 |
| 22 | 10 | 10 |
| Hatched 22-23 | 8+ | 8 |

+Five chicks were healthy

Early losses are compounded, on the fourth day, of embryos that failed to develop, and on the tenth day, of embryos damaged during transfer from systems II to III. Embryos cultured from fertilised ova were fragile and more susceptible to damage than embryos cultured from day 1. The hatch rate was 8% and approximately half the number of hatchlings were healthy. At a high humidity, R.H. 50-60%, the hatch rate was similar (n=85), but only one hatchling was healthy. One weak chick hatched from cultures incubated at R.H. 60-75%.

In total, 7 healthy chicks were hatched from cultured fertilised ova, including one that was cultured by a modified method. Two cockerels have survived to maturity; one is fertile, giving a hatch rate of 75% from eggs of inseminated Warren hens, and the other is infertile. Two 9 week-old pullets appear healthy. The remaining birds survived for 1, 8 and 16 weeks, respectively.

The reasons for adopting 3 distinct culture systems for successive periods of development have been discussed above. It appears that the superstratum plays a crucial role in the growth of the embryos. The proper relationship of the embryo with the superstratum was determined empirically, and appropriate adjustments were made in the design of the culture chamber to accommodate the changing requirements at different phases of embryonic development. In Phase I, an excess of medium above the embryo was detrimental, and in Phase II it was essential for growth. An excess of medium was not harmful in Phase III until day 8, when development was arrested unless the vascular extraembryonic membranes were exposed to the atmosphere in the chamber.

The linkage of systems I to II to III, to support growth of the chick embryo in culture from a stage shortly after fertilisation to hatch is itself a new procedure. This is the first report of a complete culture system for the avian embryo (Perry, 1988).

The establishment of a complete in vitro system for the chick embryo has a wide range of potential applications in areas of basic and applied research. It provides the opportunity to manipulate the avian ovum by, for example, the injection of foreign genes or whole genomes, and to investigate the effects of such manipulations in the hatched chick and probably in the mature bird. The methods also give guidelines for devising in vitro techniques for oviductal embryos at earlier and more advanced stages than those presently employed, with applications in the fields of in vitro fertilisation and the insertion of putative totipotent cells into the embryo.

A potential application is in the production of transgenic poultry. Modifications of the factors for growth and reproductive performance will be of benefit to the poultry industry. Furthermore, the insertion of genes for novel proteins into the avian germ line is a potentially valuable technique for the production of biomedically important proteins in egg white. The high reproductive capacity of the domestic fowl gives it an advantage over other farm animals in this technological field. A hen matures in 6 months and is capable of producing some 300 eggs in the first year of lay.

In summary, separate culture systems have been devised for the 3 phases of development, the embryos being transferred from one system to the next to cover the total embryonic life-span. The overall experimental design and order of the techniques are shown in diagrammatic form in FIG. 1. The exemplified method for Phase III is a discrete system (Example 1). The exemplified method for Phase II overlaps that for Phase III (Example 2), but transfer between these systems should for preference be made at a specific stage due to the increased fragility of the embryo with age (Example 3). The method for Phase I covers a period commencing some 2 h after ovulation, when albumen deposition is underway and the male and female pronuclei are undergoing enlargement (Perry, 1987). It requires linkage with the method for Phase II for its analysis (Example 4) and, subsequently, with the method for Phase III for a complete culture system (Example 5).

REFERENCES

Beadle, B. W., Conrad, R. M. and Scott, H. M. (1938). Composition of the uterine secretion of the domestic fowl. *Poultry Sci.* 17: 498-504.

Callebaut, M. (1983). Autoradiographic demonstration of the penetration of albumen-derived material through the vitelline membrane into the egg yolk, exterior to the avian blastoderm. *Poultry Sci.* 2:1657-1659.

Crittenden, L. B. and Salter, D. W. (1986). Gene insertion and long-term goals. *Avian Diseases*, 30:43-46.

Davidson, M. F. and Draper, M. H. (1969). The accumulation of glucose in the white of the egg of the hen. *J. Physiol.* 202: 119-120p.

Dawes, C. H. (1975). Acid-base relationships within the avian egg. *Biol. Rev.* 50:351-371.

Dunn, B. E., Fitzharris, T. P. and Barnett, B. D. (1981). Effects of varying chamber construction and embryo pre-incubation age on survival and growth of chick embryos in shell-less culture. *Anat. Rec.* 199 : 33-43.

Freeman, B. M. and Messer, L. I. (1985). Genetic manipulation of the domestic fowl—a review. *World's Poultrt Science Journal* 41: 124-132.

Hamburger, V. and Hamilton, H. L. (1951). A series of normal stages in the development of the chick embryo. *J. Morph.* 88:49-67.

Howarth, B. (1971). An examination of sperm capacitation in the fowl. *Biol. Reprod.* 3 : 338-341.

Kochav, S. and Eyal-Giladi, H. (1971). Bilateral symmetry in chick embryo determination by gravity. *Science.* 171 : 1027-1029.

Kochav, S., Ginsburg, M. and Eyal-Giladi, H. (1980). From cleavage to primitive streak formation a complementary normal table and a new look at the first stages of development of the chick. II. Microscopic anatomy and cell population dynamics. *Dev. Biol.* 79: 296-308.

Leonard, E. M. (1968). The accumulation of minerals in the avian oviduct. Ph.D. Thesis, Univ. of Edinburgh.

New, D. A. T. (1956). The formation of the sub-blastodermic fluid in the hens, egg. *J. Embryol. exp. Morph.* 4:221-227.

New, D. A. T. (1957). A critical period for the turning of hens, eggs. *J. Embryol. exp. Morph.* 5: 293-299.

New, D. A. T. (1966). "The culture of vertebrate embryos". London : Academic Press.

Olszanska, B., Szolajska, E. and Lassota, Z. (1984). Effect of spatial position of uterine quail blastoderms cultured in vitro on bilateral symmetry formation. *Roux's Arch. Dev. Biol.* 193:108-110.

Ono, T. and Wakasugi, N. (1984). Mineral content of quail embryos cultured in mineral-rich and mineral-free conditions. *Poultry Sci.* 63: 159-166.

Perry, M. M. (1986a). Embryo manipulation in poultry. Proc. XXVII. *Br. Poultry Breeders' Roundtable.*

Perry, M. M. (1986b). Embryo manipulation in poultry. Edinburgh Centre for Rural Economy. Annual report, 1985-86, 19-24

Perry, M. M. (1987). Nuclear events from fertilisation to the early cleavage stages in the domestic fowl. (*Gallus domesticus*). *J. Anat.* 150, 99-109.

Perry, M. M. (1988). A complete culture system for the chick embryo. *Nature,* 331, 70-72.

Romanoff, A. L. (1943). Cultivation of the early chick embryo in vitro. *Anat. Rec.* 87 : 365-369.

Rowlett, K. and Simkiss, K. (1985). The surrogate egg. *New Scientist,* 1469:42-44.

Rowlett, K. and Simkiss, K. (1987). Explanted embryo culture in vitro and in ovo techniques for domestic fowl. *Br. Poultry Sci.* 28:9-101.

Sauveur, B. and Mongin, P. (1971). Etude comparative du fluide uterine et de l'albumen de l'oeuf in utero chez le poule. *Ann. Biol. anim. Bioch. Biophys.* 11:213-224.

Wangensteen, O. D. and Rahn, H. (1970/71). Respiratory gas exchange by the avian embryo. *Respir. Physiol.* 11, 31-45.

I claim:

1. A process for the in vitro culture of an avian embryo up to blastoderm formation, during embryonic morphogenesis and during embryonic growth to hatch, the process comprising culturing an avian embryo by a process comprising culturing a fertilized avian ovum, having a surrounding capsule of dense albumen, partially subemreged in culture medium in a first container sealed with a film having low gas permeability and not naturally associated with an resultant avian egg, up to blastoderm formation, subsequently culturing the avian embryo by a process comprising incubating said avian embryo during embryonic mrophogenesis in a culture medium in a liquid-filled liquid-impermeable second container sealed with a partially gas permeable film, and subsequently culturing the resultant avian embryo by a process comprising incubating said avian embryo during the embryonic growth phase in a closed second or third container, there being an air space above the embryo, the air space being separated from the external atmosphere by a partially gas permeable film, said incubating continuing until said embryo hatches.

* * * * *

UNITED STATES PATENT AND TRADEMARK OFFICE
CERTIFICATE OF CORRECTION

PATENT NO. : 5,011,780

DATED : April 30, 1991

INVENTOR(S) : Margaret M. Perry

Page 1 of 4

It is certified that error appears in the above-identified patent and that said Letters Patent is hereby corrected as shown below:

Title page, item,

| | | |
|---|---|---|
| [56] Publications | 4th Ref. | "Hens's" should be --Hens'-- |
| [56] | 5th Ref. | "News" should be --New-- |
| [56] | 10th Ref. | "L'albument" should be --l'albumen-- |
| [56] | 11th Ref. | "Flow" should be fowl |
| [56] | 14th Ref. | "Developement" should be --Development-- |
| [56] | 16th Ref. | "Viteline" should be --Vitelline-- |
| [56] | 17th Ref. | "ulte-rine" should be --uterine-- |
| Column 2, line 48, | | "morphogeneiss" should be --morphogenesis-- |
| Column 3, line 5, | | "or" should be --on-- |
| Column 3, line 6, | | "period" should be --periods-- |
| Column 3, line 11, | | "egg" should be --egg 1-- |
| Column 3, line 11, | | "hen;" should be --hen, wherein the following reference numerals apply: 2, shell; 4, outer shell membrane; 6, air space; 8, inner shell membrane; 10, albumen; 12, outer liquid layer; 14, dense layer; 16, inner liquid layer; 18, chalazipherous layer; 20, chalaza; 22, vitelline membrane; 24, yolk; and 26, blastoderm;-- |
| Column 3, line 12, | | "system" should be --system 28-- |

UNITED STATES PATENT AND TRADEMARK OFFICE
CERTIFICATE OF CORRECTION

PATENT NO. : 5,011,780

DATED : April 30, 1991

INVENTOR(S) : Margaret M. Perry

It is certified that error appears in the above-identified patent and that said Letters Patent is hereby corrected as shown below:

| Column | Line | |
|---|---|---|
| 3 | 13 | "hatch);" should be -- hatch), wherein the following reference numerals apply: 30, embryo; 32, culture medium; 34, recipient shell; 36, air space; and 38, cling film;-- |
| 3 | 14 | "system" should be --system 40-- |
| 3 | 15 | "9);" should be --9), wherein the following reference numberals apply: 42, embryo; 44, capsule of dense albumen; 46, culture medium; 48, recipient shell; 50, cling film seal; 42, holding ring; and 54, elastic band; and-- |
| 3 | 16 | "system" should be --system 56-- |
| 3 | 17 | "1)." should be --1), wherein the following reference numerals apply: 58, germinal disc; 60, capsul of dense albumen; 62, culture medium; 64, glass jar; and 66, low gas permeability film.-- |
| 3 | 36-37 | "permeabiIlty" should be --permeability-- |
| 3 | 65 | "between-the" should be --between the-- |
| 5 | 36-37 | "permeabiIity" should be --permeability-- |
| 5 | 37-38 | "5mg/cm$^2$/24h" should be --5mg/cm$^2$/24h-- |
| 6 | 1 | "of to 2" should be --of 1 to 2-- |

UNITED STATES PATENT AND TRADEMARK OFFICE
CERTIFICATE OF CORRECTION

PATENT NO. : 5,011,780

DATED : April 30, 1991

INVENTOR(S) : Margaret M. Perry

It is certified that error appears in the above-identified patent and that said Letters Patent is hereby corrected as shown below:

| Column | Line | |
|---|---|---|
| 6 | 34 | "vaculoated" should be --vacuolated-- |
| 6 | 64 | after "initially" delete "30" |
| 7 | 29 | after "Ltd)." start a new paragraph with "Sterility" |
| 9 | 1 | "sub]ect" should be --subject-- |
| 9 | 43 | "]ar" should be --jar-- |
| 9 | 54 | after "hooked" deleted "0" |
| 9 | 58 | after "90°" insert --in-- |
| 11 | 20 | "Example" should be --Example 1-- |
| 12 | 8 | after "viscous" delete "25" |
| 12 | 27 | "part)" should be --(1 part)-- |
| 12 | 29 | "$MgCl_2.6H_20$" should be --$MgCl_2.6H_20$-- |
| 12 | 29 | "$CaCl_2.2H_20$" should be --$CaCl_2.2H_20$-- |
| 12 | 40 | "accura.te" should be --accurate-- |
| 14 | 44 | after "with" insert --SARAN-- |
| 14 | 46 | "Was" should be --was-- |
| 14 | 54-55 | "cultured'" should be --cultured-- |
| 15 | 20 | "into a" should be --into an-- |
| 15 | 47 | "4 days," should be --4 days'-- |
| 16 | 56 | "is.the" should be --is the-- |

UNITED STATES PATENT AND TRADEMARK OFFICE
CERTIFICATE OF CORRECTION

PATENT NO. : 5,011,780

DATED : April 30, 1991

INVENTOR(S) : Margaret M. Perry

It is certified that error appears in the above-identified patent and that said Letters Patent is hereby corrected as shown below:

| Column | Line | |
|---|---|---|
| 17 | 41 | "2:1657-1659" should be --62:1657-1659-- |
| 17 | 55 | "Poultrt" should be --Poultry-- |
| 18 | 7 | "hens," should be --hens'-- |
| 18 | 10 | "hens," should be --hens'-- |
| 18 | 36 | "28:9-101" should be --28:91-101-- |
| 18 (Claim 1, Line 7) | 51 | "subemreged" should be --submerged-- |
| 18 (Claim 1, Line 9) | 53 | after "an" delete "resultant" |
| 18 (Claim 1, Line 10) | 54 | after "the" insert --resultant-- |
| 18 (Claim 1, Line 12) | 56 | "mrophogenesis" should be --morphogenesis-- |

Signed and Sealed this

Twenty-second Day of June, 1993

Attest:

MICHAEL K. KIRK

*Attesting Officer*      *Acting Commissioner of Patents and Trademarks*